(12) United States Patent
Yu et al.

(10) Patent No.: US 9,845,236 B2
(45) Date of Patent: Dec. 19, 2017

(54) MONOLITHIC MEMS PLATFORM FOR INTEGRATED PRESSURE, TEMPERATURE, AND GAS SENSOR

(71) Applicant: Taiwan Semiconductor Manufacturing Co., Ltd., Hsin-Chu (TW)

(72) Inventors: Shao-Chi Yu, Hsinchu (TW); Chia-Ming Hung, Taipei (TW); Hsin-Ting Huang, Bade (TW); Hsiang-Fu Chen, Zhubei (TW); Allen Timothy Chang, Hsinchu (TW); Wen-Chuan Tai, Hsinchu (TW)

(73) Assignee: Taiwan Semiconductor Manufacturing Co., Ltd., Hsin-Chu (TW)

(*) Notice: Subject to any disclaimer, the term of this patent is extended or adjusted under 35 U.S.C. 154(b) by 364 days.

(21) Appl. No.: 14/645,826

(22) Filed: Mar. 12, 2015

(65) Prior Publication Data

US 2016/0266061 A1    Sep. 15, 2016

(51) Int. Cl.
*B81C 1/00* (2006.01)
*G01L 19/00* (2006.01)
(Continued)

(52) U.S. Cl.
CPC ............ *B81C 1/00269* (2013.01); *B81B 7/02* (2013.01); *G01K 13/00* (2013.01); *G01L 9/0073* (2013.01);
(Continued)

(58) Field of Classification Search
CPC . G01L 9/0073; G01L 19/0092; G01N 27/126; G01N 27/221; G01N 2027/222;
(Continued)

(56) References Cited

U.S. PATENT DOCUMENTS

| 6,046,492 A * | 4/2000 | Machida ............. H01L 27/0825 257/467 |
| 2016/0023888 A1* | 1/2016 | Quevy ................ B81C 1/00285 257/414 |

OTHER PUBLICATIONS

Hsu. "Chapter 2 Working Principles of MEMS and Microsystems." Lectures on MEMS and Microsystems Design and Manufacture. 2008.
(Continued)

*Primary Examiner* — Paul West
(74) *Attorney, Agent, or Firm* — Eschweiler & Potashnik, LLC (57) ABSTRACT

The present disclosure is directed to a monolithic MEMS (micro-electromechanical system) platform having a temperature sensor, a pressure sensor and a gas sensor, and an associated method of formation. In some embodiments, the MEMS platform includes a semiconductor substrate having one or more transistor devices and a temperature sensor. A dielectric layer is disposed over the semiconductor substrate. A cavity is disposed within an upper surface of the dielectric layer. A MEMS substrate is arranged onto the upper surface of the dielectric layer and has a first section and a second section. A pressure sensor has a first pressure sensor electrode that is vertically separated by the cavity from a second pressure sensor electrode within the first section of a MEMS substrate. A gas sensor has a polymer disposed between a first gas sensor electrode within the second section of a MEMS substrate and a second gas sensor electrode.

20 Claims, 9 Drawing Sheets

(51) Int. Cl.
 B81B 7/02 (2006.01)
 G01L 9/00 (2006.01)
 G01K 13/00 (2006.01)
 G01N 27/22 (2006.01)
(52) U.S. Cl.
 CPC ........ *G01L 19/0092* (2013.01); *G01N 27/221* (2013.01); *B81B 2201/0214* (2013.01); *B81B 2201/0264* (2013.01); *B81B 2201/0278* (2013.01); *B81B 2207/096* (2013.01); *B81C 2203/0109* (2013.01); *G01N 2027/222* (2013.01)
(58) Field of Classification Search
 CPC .................... G01N 27/227; B81B 7/02; B81B 2201/0214; B81B 2201/0221
 See application file for complete search history.

(56) References Cited

OTHER PUBLICATIONS

Bai, et al. "Gas Sensors Based on Conducting Polymers." Sensors 2007, 7, 267-307. Mar. 7, 2007.
Riley. "Under Bump Metallization (UBM)." Sep. 2001. Retrieved from http://www.flipchips.com/tutorial/process/under-bump-metallization-ubm/.

* cited by examiner

MONOLITHIC MEMS PLATFORM FOR INTEGRATED PRESSURE, TEMPERATURE, AND GAS SENSOR

BACKGROUND

MEMS (micro-electromechanical system) devices have found widespread use in many modern day electronic devices. For example, MEMS devices are commonly found in automobiles (e.g., in airbag deployment systems), tablet computers, or in smart phones. In recent years, it is increasingly common for Micro-Electro-Mechanical Systems (MEMS) to be incorporated into integrated chips formed by a complementary metal-oxide-semiconductor (CMOS) process. The incorporation of MEMS (e.g., sensors, integrated optics, biochips, etc.) into an integrated chip formed by a CMOS process allows for widespread use of MEMS fabricated with a high throughput.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 8-14 illustrate some embodiments of cross-sectional views showing a method of forming an integrated chip comprising a monolithic MEMS platform having a pressure sensor, a temperature sensor, and a gas sensor.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Modern day electronic devices often comprise a plurality of sensing elements that act to provide different information to a common processor within a CMOS substrate (i.e., a substrate having logic devices formed by a CMOS process). Some such sensing elements may be easily integrated into the CMOS substrate. For example, temperature sensors may be formed within a CMOS substrate according to a traditional CMOS process. However, MEMS devices often comprise structural components that are not present in CMOS processes. Therefore, MEMS devices and CMOS substrates are often formed on separate substrates (i.e., die), which are laterally arranged next to each other on a printed circuit board (PCB) within a package. The separate substrates are electrically connected to one another by one or more bonding wires.

It has been appreciated that sensor systems with multiple die arranged within a shared package have a number of drawbacks. For example, these sensor systems have a relatively large form factor (i.e., size). Furthermore, because the sensing elements are formed on separate substrates, the fabrication and packaging processes of such sensor systems add additional complexity and cost.

Accordingly, the present disclosure is directed to a monolithic MEMS (micro-electromechanical system) platform comprising a temperature sensor, a pressure sensor, and a gas sensor arranged within a shared semiconductor die, and an associated method of formation. In some embodiments, the monolithic MEMS platform comprises a semiconductor substrate comprising one or more transistor devices and a temperature sensor. A dielectric layer is disposed over the semiconductor substrate. A MEMS substrate comprising a doped semiconductor material is arranged over the dielectric layer. The MEMS substrate comprises a second pressure sensor electrode electrically disconnected from a laterally adjacent first gas sensor electrode. A cavity disposed within an upper surface of the dielectric layer is configured to vertically separate the second pressure sensor electrode from a first pressure sensor electrode to form a MEMS pressure sensor. A polymer is disposed between the first gas sensor electrode and a second gas sensor electrode to form a MEMS gas sensor. By forming the temperature sensor, the gas sensor, and the pressure sensor within a shared semiconductor die, the disclosed monolithic MEMS platform provides for a low cost sensor system with a small form factor.

Figure 1A:
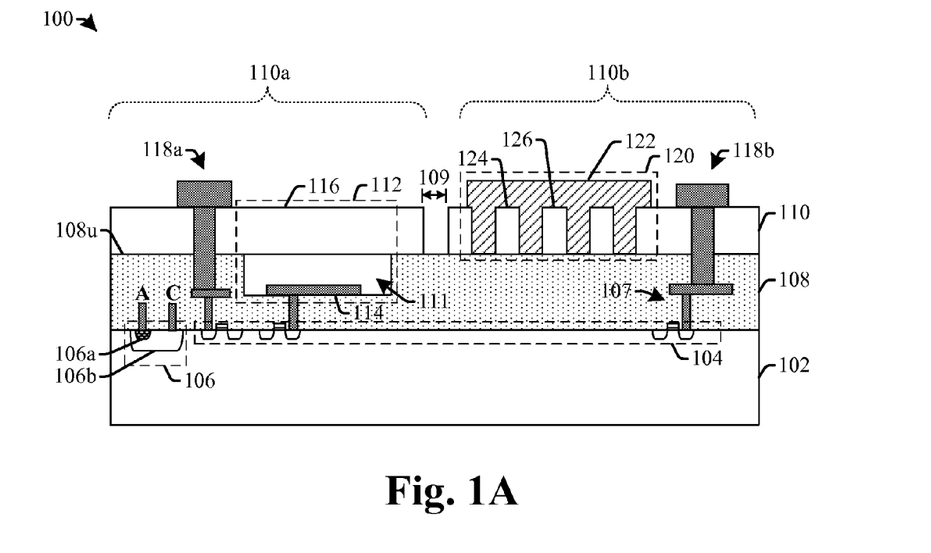
FIGS. 1A-1B illustrate some embodiments of a monolithic MEMS platform having a pressure sensor, a temperature sensor, and a gas sensor.
Figure 1B:
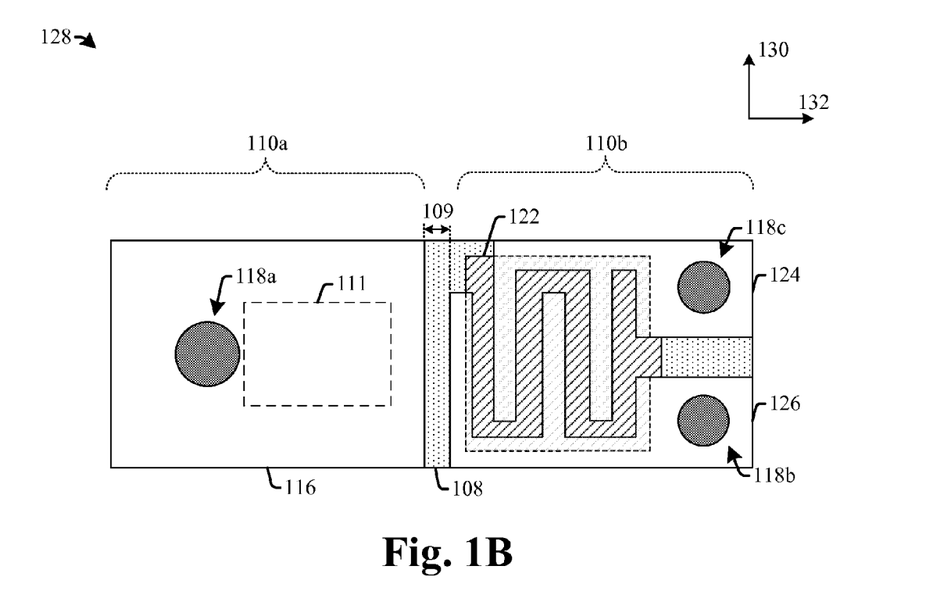

FIGS. 1A-1B illustrate some embodiments of a monolithic MEMS platform 100 having a pressure sensor, a temperature sensor, and a gas sensor.

The monolithic MEMS platform 100 comprises a semiconductor substrate 102 containing a plurality of semiconductor devices 104 (e.g., MOSFET devices). A dielectric layer 108 is arranged over the semiconductor substrate 102. A cavity 111 is disposed within an upper surface 108u of the dielectric layer 108. A MEMS substrate 110 is arranged over the dielectric layer 108. In some embodiments, the MEMS substrate 110 comprises a conductive doped semiconductor material (e.g., doped amorphous silicon or doped polycrystalline silicon). The MEMS substrate 110 has a first section 110a and a second section 110b, which is laterally adjacent to the first section 110a. The first section 110a is electrically disconnected from the second section 110b by a space 109.

The monolithic MEMS platform 100 comprises a temperature sensor 106, a pressure sensor 112, and a gas sensor 120. The temperature sensor 106 is disposed within the semiconductor substrate 102. The pressure sensor 112 is located over the semiconductor substrate 102 at a first position. The gas sensor 120 is located over the semiconductor substrate 102 at a second position that is laterally displaced from the first position.

The temperature sensor 106 may be any suitable type of temperature sensor. In some embodiments, the temperature sensor 106 includes one or more diodes. For example, the temperature sensor 106 may include at least one P-N junction comprising a first diode region 106a having a first doping type (e.g., p-type) and a second diode region 106b having an opposite second doping type (e.g., n-type). In some embodiments, the temperature sensor 106 may comprise a dual diode temperature sensor including two diodes. In some embodiments, the two diodes of temperature sensor 106 are configured to be operated at different current densities for proportional to absolute temperature (PTAT) temperature sensing. In other embodiments, the temperature sensor 106 may comprise a resistor (e.g., a shallow diffusion resistor or a well diffusion resistor comprising a doped region of semiconductor substrate 102). In such embodiments, a temperature can be measured according to a relationship between resistance and temperature.

The pressure sensor 112 comprises a first pressure sensor electrode 114 and a second pressure sensor electrode 116 that is vertically separated from the first pressure sensor electrode 114 by the cavity 111. In some embodiments, the first pressure sensor electrode 114 comprises a first metal interconnect structure located on a bottom surface of the cavity 111. The second pressure sensor electrode 116 is disposed over the cavity 111 and may hermetically seal the cavity 111 at a predetermined pressure. In some embodiments, the second pressure sensor electrode 116 comprises the first section 110a of the MEMS substrate 110.

The first pressure sensor electrode 114 is electrically connected to one or more of the semiconductor devices 104 within the semiconductor substrate 102 by way of one or more metal interconnect layers (e.g., vias and/or metal wire layers). The second pressure sensor electrode 116 is electrically connected to one or more of the semiconductor devices 104 within the semiconductor substrate 102 by way of a vertical interconnect structure 118a having a through-substrate-via (TSV) that extends through the MEMS substrate 110 and one or more underlying metal interconnect layers 107. In some embodiments, the vertical interconnect structure 118a may extend to a position abutting the upper surface of the MEMS substrate 110 so as to form an improved electrical connection with the MEMS substrate 110.

During operation of the pressure sensor 112, the second pressure sensor electrode 116 will bend or deflect in response to a change in pressure in an ambient environment. As the second pressure sensor electrode 116 bends, a distance changes between the first pressure sensor electrode 114 and the second pressure sensor electrode 116. The change in distance causes a change in capacitance between the pressure sensor electrodes, which can be measured by the semiconductor devices 104 within the semiconductor substrate 102 to determine a pressure of a gas abutting the second pressure sensor electrode 116.

The gas sensor 120 comprises a polymer 122 disposed between a first gas sensor electrode 124 and a second gas sensor electrode 126. In some embodiments, the first gas sensor electrode 124 and the second gas sensor electrode 126a comprise the second section 110b of the MEMS substrate 110. The first gas sensor electrode 124 and the second gas sensor electrode 126 are electrically connected to one or more semiconductor devices 104 within the semiconductor substrate 102 by way additional vertical interconnections 118b, 118c respectively comprising a TSV that extends through the MEMS substrate 110 and one or more underlying metal interconnect layers 107. As shown in top-view 128, the polymer 122 may be disposed between the first gas sensor electrode 124 and the second gas sensor electrode 126 in a first direction 130 and in a perpendicular second direction 132. In some embodiments, the first gas sensor electrode 124 and the second gas sensor electrode 126 comprise comb-like structures. For example, the first gas sensor electrode 124 may comprise a first comb-like structure and the second gas sensor electrode 126 may comprise a second comb-like structure inter-digitated with the first comb-like structure.

The polymer 122 has a dielectric constant that changes in the presence of a liquid and/or gas within the ambient environment. For example, the dielectric constant of the polymer 122 may change depending on a presence of water (e.g., humidity) or other liquids, and/or in the presence of a gas. During operation of the gas sensor 120, a capacitance between the first gas sensor electrode 124 and the second gas sensor electrode 126 can be measured. Since the dielectric constant of the polymer 122 changes in the presence of a liquid (i.e., humidity), the capacitance of the gas sensor 120 will change in the presence of the liquid, thereby allowing the gas sensor 120 to measure a humidity of the ambient environment.

By forming the temperature sensor 106, the pressure sensor 112, and the gas sensor 120 within a monolithic substrate, the monolithic MEMS platform 100 is able to provide a relatively small form factor (e.g., a form factor smaller than systems in which the devices are disposed onto separate substrates).

Figure 2A:
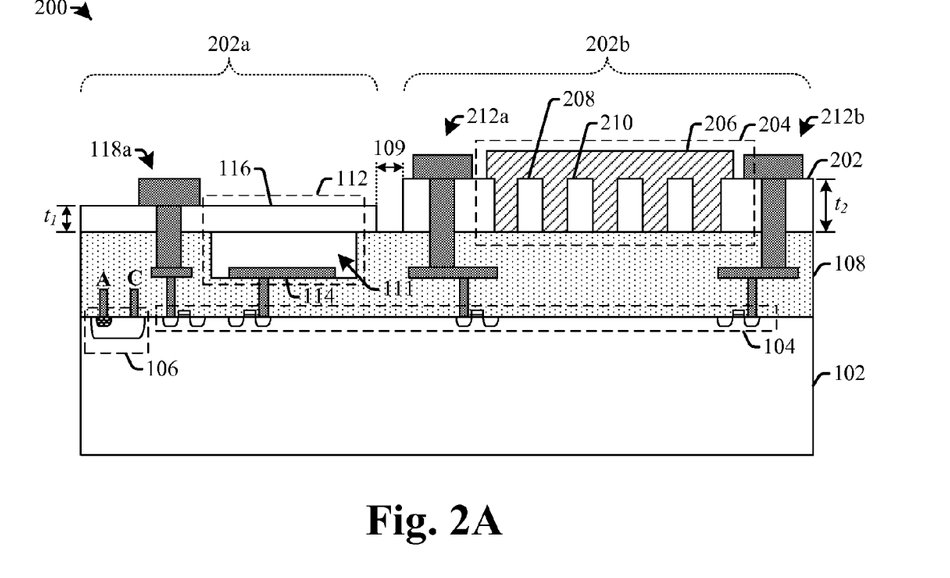
FIGS. 2A-2B illustrate some additional embodiments of a monolithic MEMS platform having a pressure sensor, a temperature sensor, and a gas sensor.
Figure 2B:
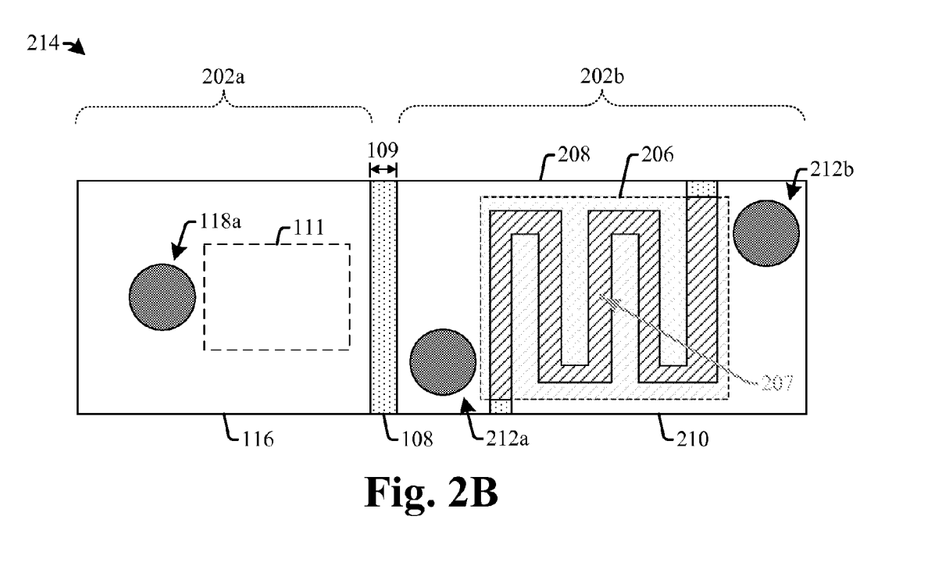

FIGS. 2A-2B illustrate some additional embodiments of a monolithic MEMS platform 200 having a pressure sensor, a temperature sensor, and a gas sensor.

The monolithic MEMS platform 200 comprises a MEMS substrate 202 having a first section 202a and a second section 202b, which is laterally adjacent to the first section 202a. The first section 202a is electrically isolated from the second section 202b. The first section 202a has a first thickness $t_1$, and the second section 202b has a second thickness $t_2$ that is different than the first thickness $t_1$. In some embodiments, the first thickness $t_1$ may be less than the second thickness $t_2$.

The monolithic MEMS platform 200 comprises a gas sensor 204 including a first gas sensor electrode 208 having a first comb-like structure and a second gas sensor electrode 210 having a second comb-like structure. As shown in top-view 214, the first and second comb-like structures are arranged in a point like reflection about an origin 207 disposed therebetween (e.g., the first comb-like structure has a same shape as the second comb-like structure, but is rotated by) 180°. A polymer 206 is disposed over and between the first and second gas sensor electrodes, 208 and 210.

The first gas sensor electrode 208 is connected to one or more semiconductor devices 104 within the semiconductor substrate 102 by way of a second vertical interconnect structure 212a and the second gas sensor electrode 210 is connected to one or more semiconductor devices 104 within the semiconductor substrate 102 by way of a third vertical interconnect structure 212b. The second vertical interconnect structure 212a is separated from the third vertical interconnect structure 212b in a first direction and in a perpendicular second direction.

Figure 3A:
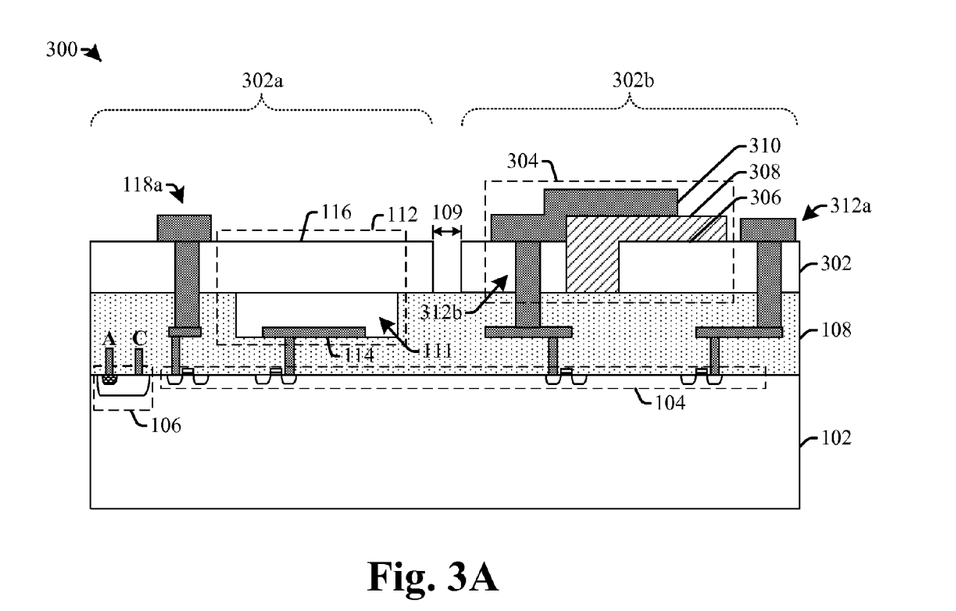
FIGS. 3A-3B illustrate some additional embodiments of a monolithic MEMS platform having a pressure sensor, a temperature sensor, and a gas sensor.
Figure 3B:
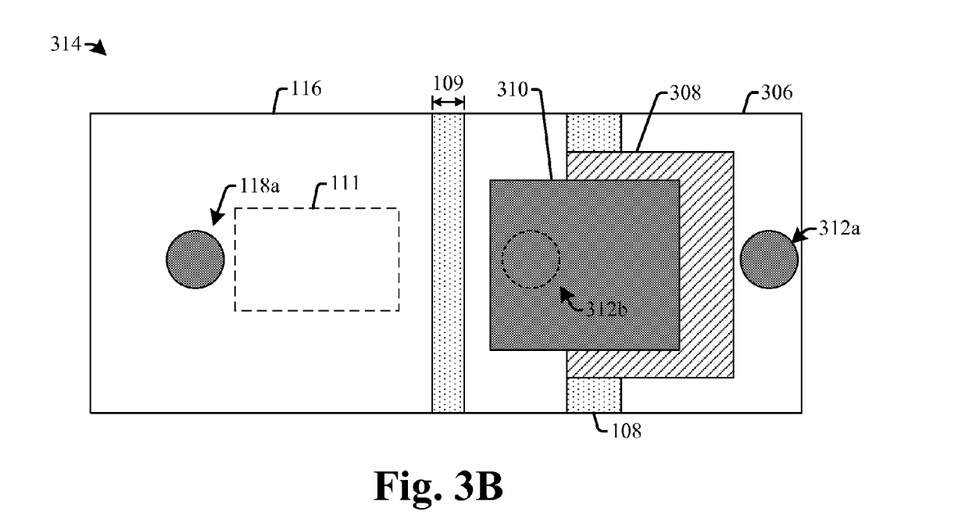

FIGS. 3A-3B illustrate some additional embodiments of a monolithic MEMS platform 300 having a pressure sensor, a temperature sensor, and a gas sensor.

The monolithic MEMS platform 300 comprises planar gas sensor 304 comprising a first gas sensor electrode 306 vertically separated from a second gas sensor electrode 310 by a polymer 308. In some embodiments, the first gas sensor electrode 306 comprises a second section 302b of the MEMS substrate 302, which is electrically isolated from a laterally adjacent first section 302a of the MEMS substrate 302. In some embodiments, the second gas sensor electrode 310 comprises a metal material disposed over the MEMS substrate 302 and the polymer 308. As shown in top-view 314, the first gas sensor electrode 306, the second gas sensor electrode 310, and the polymer 308 have substantially rectangular shapes.

In some embodiments, the polymer 308 may extend within a recess within the second section 302b of the MEMS substrate 302, which is disposed between the first gas sensor electrode 306 and the second gas sensor electrode 310. In such embodiments, the first gas sensor electrode 306 and the second gas sensor electrode 310 are also laterally separated from one another. In such embodiments, the second gas sensor electrode 310 may further comprise the second section 302b of the MEMS substrate 302.

Figure 4:
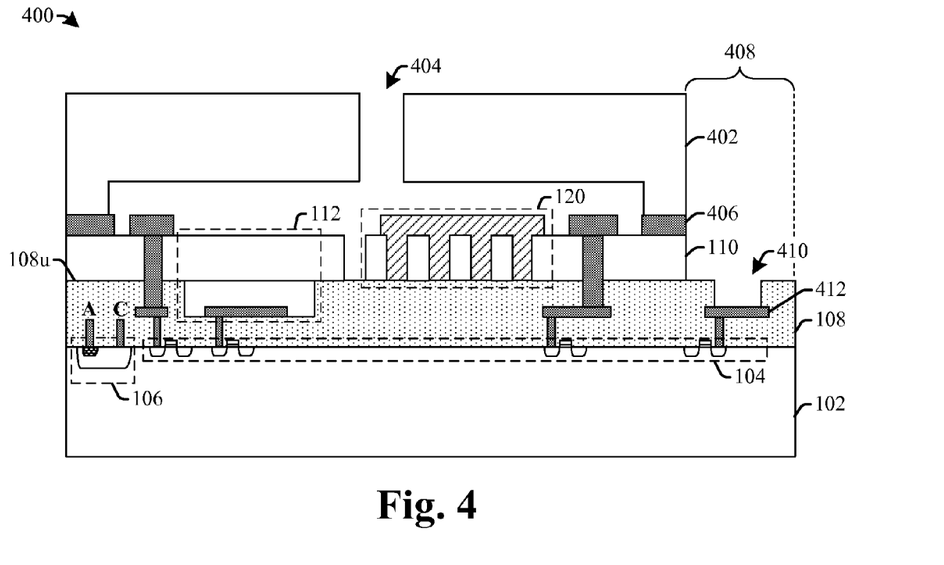
FIG. 4 illustrates a cross-sectional view of some embodiments of a disclosed monolithic MEMS platform having a wafer level package (WLP).

FIG. 4 illustrates a cross-sectional view of some embodiments of a disclosed monolithic MEMS platform 400 having a wafer level package (WLP).

The monolithic MEMS platform 400 comprises a capping substrate 402 disposed over a MEMS substrate 110. In some embodiments, a bonding interface layer 406 may be configured between the capping substrate 402 and the MEMS substrate 110. The capping substrate 402 comprises a cavity arranged on a side of the capping substrate 402 facing the MEMS substrate 110. An opening 404 extends through the capping substrate 402 so that the cavity is in communication with an ambient environment. In some embodiments, the capping substrate 402 may comprise a semiconductor material (e.g., silicon). In some embodiments, wherein the capping substrate 402 is connected to the MEMS substrate 110 by way of a eutectic bond, the bonding interface layer 406 layer may comprise one or more metal materials.

The MEMS substrate 110 is set back from an outer edge of the semiconductor substrate 102 and the dielectric layer 108 so as to expose a bonding area 408 having an exposed metal interconnect layer 412. In some embodiments, the exposed metal interconnect layer 412 may comprise aluminum. In some embodiments, a portion of an upper surface 108u of the dielectric layer 108 is also exposed within the bonding area 408. The upper surface 108u of the dielectric layer 108 contains a recess 410 that vertically extends from the upper surface 108u to the metal interconnect layer 412.

Figure 5:
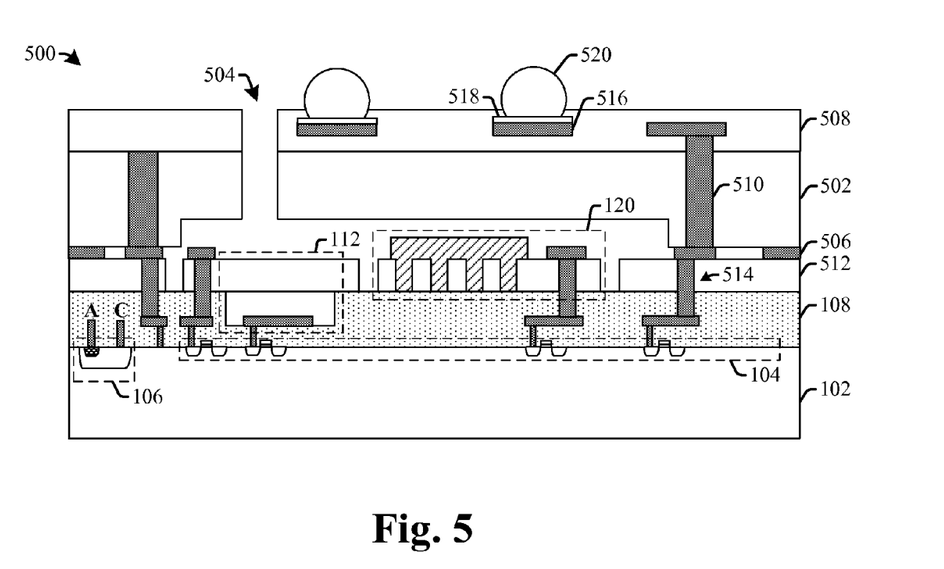
FIG. 5 illustrates a cross-sectional view of some additional embodiments of a disclosed monolithic MEMS platform having a wafer level chip scale package (WLCSP).

FIG. 5 illustrates a cross-sectional view of some additional embodiments of a disclosed monolithic MEMS platform 500 having a wafer level chip scale package (WLCSP).

The monolithic MEMS platform 500 comprises a capping substrate 502 disposed over a MEMS substrate 512. In some embodiments, a bonding interface layer 506 may be configured between the capping substrate 502 and the MEMS substrate 512. The capping substrate 502 comprises a cavity arranged on a side of the capping substrate 502 facing the MEMS substrate 512.

Sidewalls of the capping substrate 502 are substantially aligned with sidewalls of the underlying MEMS substrate 512. A protection layer 508, configured to protect the capping substrate 502 during solder bonding, is disposed onto an upper surface of the capping substrate 502. The protection layer 508 may comprise a polymer or dielectric layer. For example, a solder masking film. Sidewalls of the capping substrate 502 are substantially aligned with sidewalls of the protection layer 508. An opening 504 extends through the capping substrate 502 and the protection layer 508 to place the cavity in communication with an ambient environment.

A plurality of through-substrate-vias (TSVs) 510 vertically extending through the capping substrate 502. The plurality of TSVs 510 are connected to a vertical interconnect structure 514 extending through peripheral regions of the MEMS substrate 512 that are electrically isolated from the pressure sensor 112 and the gas sensor 120. The plurality of TSVs 510 extend from the vertical interconnect structure 514 to a redistribution layer 516 located within the protection layer 508. The redistribution layer 516 provides for an electrical connection between the plurality of TSV 510 and a plurality of solder balls 520. In some embodiments, the redistribution layer 516 may comprise a conductive metal such as aluminum, for example.

In some embodiments, an under bump metallurgy (UBM) layer 518 may be disposed between the redistribution layer 516 and the plurality of solder balls 520. The UBM layer 518 may comprise a plurality of different metal layers, such as an adhesion layer, a diffusion barrier layer, a solderable layer, and an oxidation barrier layer. In various embodiments, the UBM layer 518 may comprise one or more of chromium (Cr), copper (Cu), titanium (Ti), nickel (Ni), etc.

Figure 6:
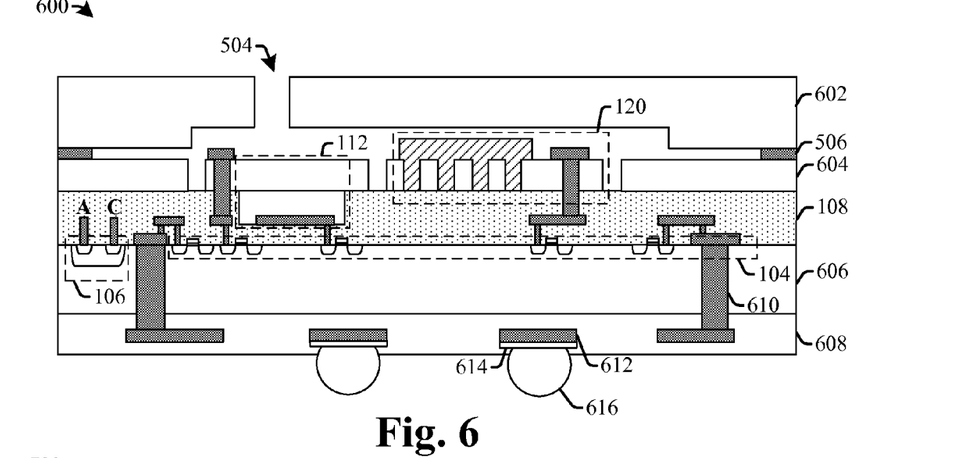
FIG. 6 illustrates a cross-sectional view of some additional embodiments of a disclosed monolithic MEMS platform having a wafer level chip scale package (WLCSP).

FIG. 6 illustrates a cross-sectional view of some additional embodiments of a disclosed monolithic MEMS platform 600 having a wafer level chip scale package (WLCSP).

The monolithic MEMS platform 600 comprises a capping substrate 602 disposed over a MEMS substrate 604. A protection layer 608 is disposed onto a lower surface of a semiconductor substrate 606. A plurality of through-substrate-vias (TSVs) 610 vertically extend through the semiconductor substrate 606 to a redistribution layer 612 located within the protection layer 608. The redistribution layer 612 provides for an electrical connection between the plurality of TSV 610 and a plurality of solder balls 616. In some embodiments, an under bump metallurgy (UBM) layer 614 may be disposed between the redistribution layer 612 and the plurality of solder balls 616.

Figure 7:
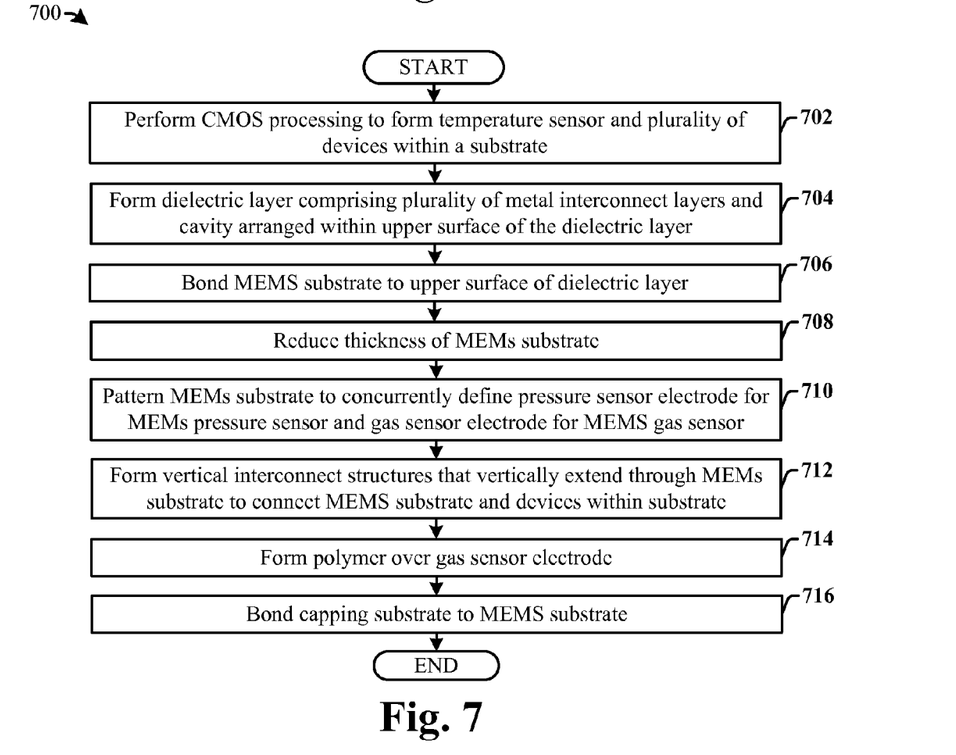
FIG. 7 illustrates a flow diagram of some additional embodiments of a monolithic MEMS platform having a pressure sensor, a temperature sensor, and a gas sensor.

FIG. 7 illustrates a flow diagram of some embodiments of a method 700 of forming a monolithic MEMS platform having a pressure sensor, a temperature sensor, and a gas sensor.

While the disclosed method 700 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 702, CMOS processing is performed to form a temperature sensor and a plurality of devices within a substrate.

At 704, a dielectric layer is formed onto the substrate. The dielectric layer has plurality of metal interconnect layers and a cavity arranged within an upper surface of the dielectric layer.

At 706, a MEMS substrate is bonded to the upper surface of the dielectric layer.

At 708, a thickness of the MEMS substrate is reduced.

At 710, the MEMS substrate is patterned to concurrently define a pressure sensor electrode for a MEMS pressure sensor and a gas sensor electrode for a MEMS gas sensor.

At 712, vertical interconnect structures are formed that vertically extend through the MEMS substrate. The conductive interconnects connect the MEMS substrate to one or more of the plurality of devices within the substrate.

At 714, a polymer is formed over the gas sensor electrode of the MEMS gas sensor.

At 716, a capping substrate is bonded to the MEMS substrate.

FIGS. 8-14 illustrate some embodiments of cross-sectional views showing a method 700 of forming an integrated chip comprising a monolithic MEMS platform having a pressure sensor, a temperature sensor and a gas sensor. Although FIGS. 8-14 are described in relation to method 700, it will be appreciated that the structures disclosed in FIGS. 8-14 are not limited to such a method, but instead may stand alone as structures independent of the method.

Figure 8:
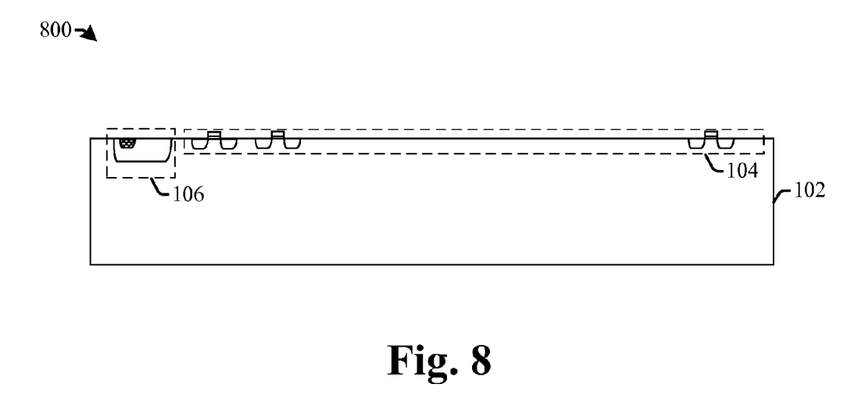

FIG. 8 illustrates some embodiments of a cross-sectional view 800 of an integrated chip corresponding to act 702.

As shown in cross-sectional view 800, a semiconductor substrate 102 is provided. The semiconductor substrate 102 may comprise any type of semiconductor body (e.g., silicon/CMOS bulk, SiGe, SOI, etc.) such as a semiconductor wafer or one or more die on a wafer, as well as any other type of semiconductor and/or epitaxial layers formed thereon and/or otherwise associated therewith.

CMOS processes are performed on the semiconductor substrate 102. The CMOS processes form a plurality of semiconductor devices 104 within the semiconductor substrate 102. The plurality of semiconductor devices 104 may comprise MOSFET (metal-oxide-silicon field effect transistor) devices. In such embodiments, the semiconductor substrate 102 is selectively implanted to form source/drain regions separated by a channel region. A gate dielectric layer and a gate electrode layer are subsequently deposited and patterned to form a gate structure overlying the channel region.

The CMOS processes also form a temperature sensor 106 within the semiconductor substrate 102. In some embodiments, the temperature sensor 106 may comprise one or more diodes. In such embodiments, the temperature sensor 106 may be formed by selectively implanting the semiconductor substrate 102 with a first dopant type to form a first diode region, and subsequently implanting the semiconductor substrate 102 with a second dopant type to form a second diode region. In other embodiments, the temperature sensor 106 may comprise a resistor. In some such embodiments, the resistor may be formed by implanting the semiconductor substrate 102 to form a shallow diffusion resistor or a well diffusion resistor. In other such embodiments, the resistor may comprise a polysilicon resistor formed by depositing and patterning polysilicon on the semiconductor substrate 102.

Figure 9:
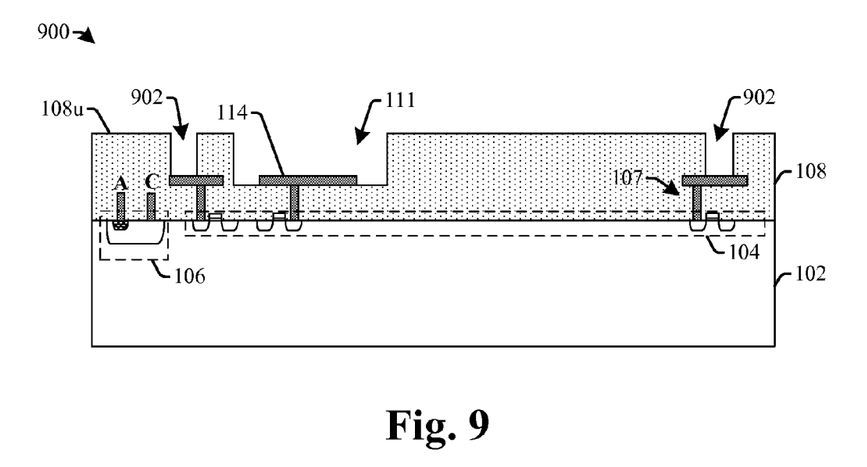

FIG. 9 illustrates some embodiments of a cross-sectional view 900 of an integrated chip corresponding to act 704.

As shown in cross-sectional view 900, a dielectric layer 108 is formed over the semiconductor substrate 102. The dielectric layer 108 may comprise one or more dielectric layers (e.g., a low-k dielectric layer, an ultra-low-k dielectric layer, a silicon oxide layer, etc.). Metal interconnect layers 107 are formed within the dielectric layer 108. The metal interconnect layers 107 are formed by selectively etching the dielectric layer 108 to form a plurality of openings and then depositing a conductive material (e.g., copper) within the one or more of the plurality of openings. The dielectric layer 108 is further etched to form a cavity 111 and a first plurality of TSV openings 902 within an upper surface 108$u$ of the dielectric layer 108. The cavity 111 may extend from the upper surface 108$u$ to a first pressure sensor electrode 114 comprising a metal wire layer located above the dielectric layer 108. In various embodiments, the dielectric layer 108 may be etched according to a dry etchant have an etching chemistry comprising a fluorine species (e.g., $CF_4$, $CHF_3$, $C_4F_8$, etc.) or a wet etchant comprising hydroflouric acid (HF), for example.

Figure 10:
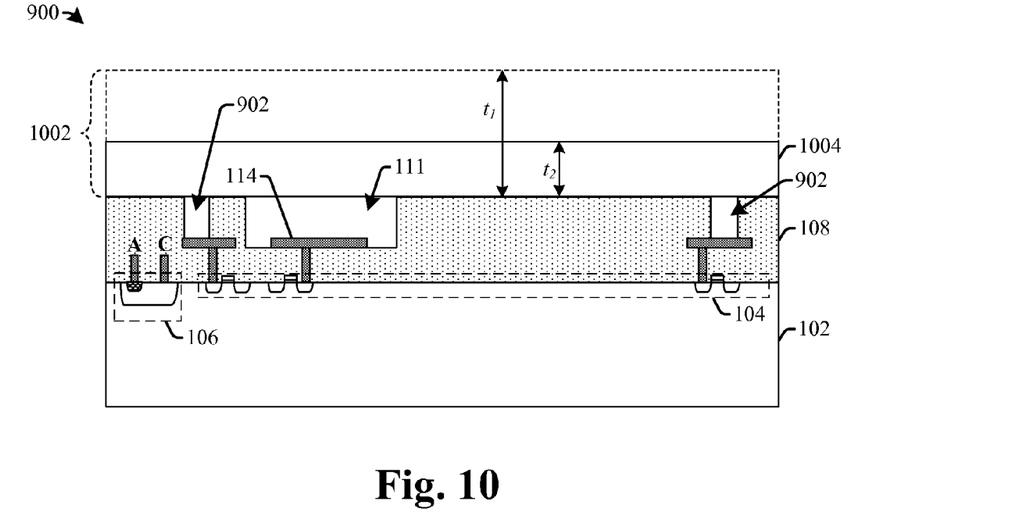

FIG. 10 illustrates some embodiments of a cross-sectional view 1000 of an integrated chip corresponding to acts 706-708.

As shown in cross-sectional view 1000, a MEMS substrate 1002 is bonded to the dielectric layer 108. In some embodiments, a direct bonding process may be used to bond the MEMS substrate 1002 to the dielectric layer 108. In other embodiments, a fusion bonding process may be used to bond the MEMS substrate 1002 to the dielectric layer 108. In some embodiments, the MEMS substrate 1002 may be bonded to the dielectric layer 108 within a processing chamber held at a predetermined pressure. Bonding the MEMs substrate 1002 to the dielectric layer 108 at the predetermined pressure will cause the cavity 111 to be sealed at the predetermined pressure. In some embodiments, the MEMS substrate 1002 may be thinned (e.g., from a first thickness $t_1$ to a second thickness $t_2$) after the bonding process to form a MEMS substrate 1004 having a reduced thickness. In some embodiments, the MEMS substrate 1004 may be thinned to a thickness in a range of between approximately 10 um and approximately 60 um.

Figure 11A:
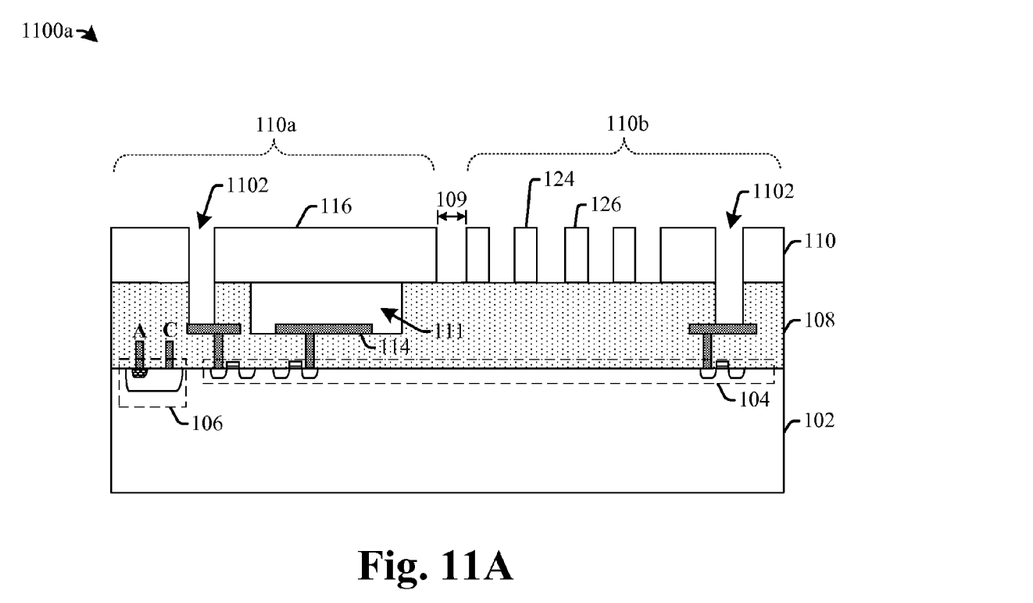
Figure 11B:
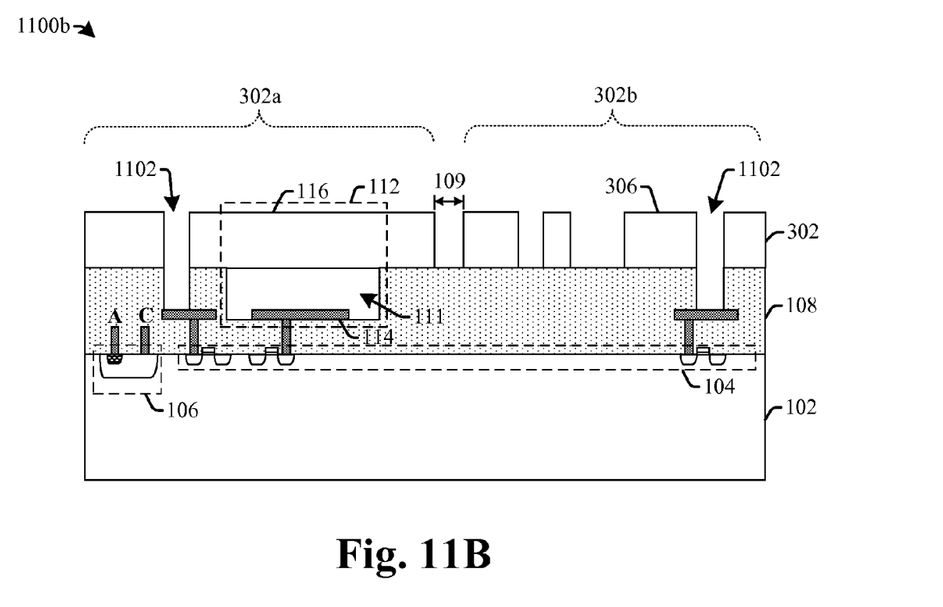

FIGS. 11A-11B illustrate some embodiments of cross-sectional views, 1100 and 1100$b$, of an integrated chip corresponding to act 710.

As shown in cross-sectional view 1100$a$, the MEMS substrate 110 is patterned to form a first section 110$a$ comprising a second pressure sensor electrode 116 and a laterally adjacent second section 110$b$ comprising one or more gas sensor electrodes, 124 and 126, comprising comb-like structures. A second plurality of TSV openings 1102, which extend through the MEMS substrate 110, are disposed over the first plurality of TSV openings 902. The first section 110$a$ is electrically disconnected from the second section 110$b$.

In some alternative embodiments, shown in cross-sectional view 1100$b$, the MEMS substrate 110 may alternatively be patterned to form a first section 110$a$ comprising a second pressure sensor electrode 116 and a laterally adjacent second section 110$b$ comprising a first gas sensor electrode 306 for a planar gas sensor (e.g., as shown in FIGS. 3A-3B).

Figure 12:
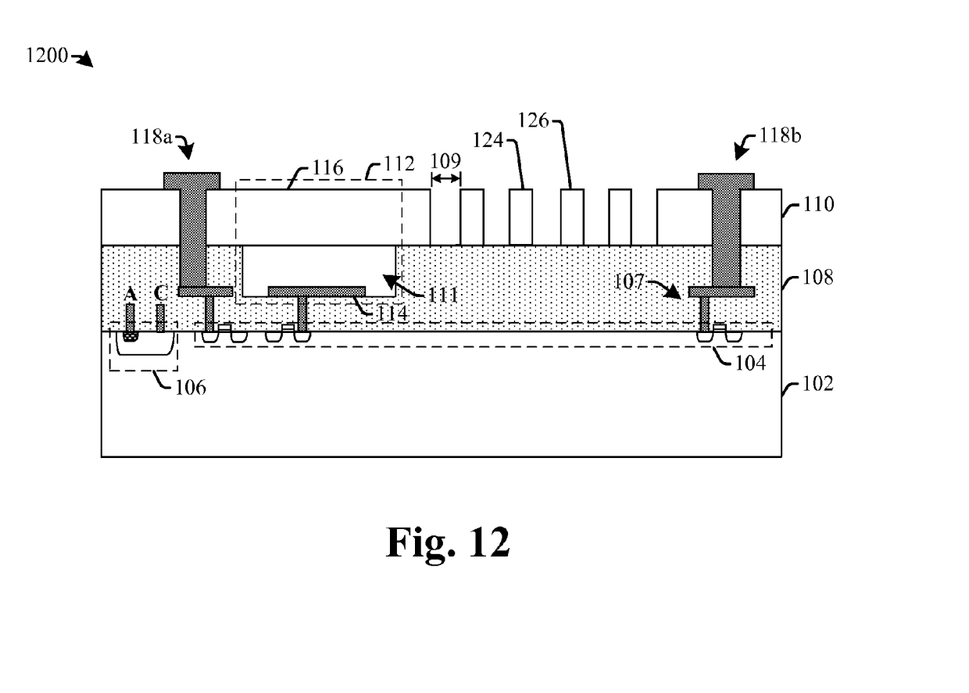

FIG. 12 illustrates some embodiments of a cross-sectional view 1200 of an integrated chip corresponding to act 712.

As shown in cross-sectional view 1200, vertical interconnect structures, 118a and 118b, are formed. The vertical interconnect structures, 118a and 118b, extend through the MEMS substrate 110 and the dielectric layer 108 to the plurality of metal interconnect layers 107. The vertical interconnect structures, 118a and 118b, may be formed by filing the first and second plurality of TSV openings, 902 and 1102, with a conductive material, such as a metal (e.g., copper, tungsten, or aluminum), using a deposition process and/or a plating process (e.g., electroplating, electroless plating, etc.).

Figure 13:
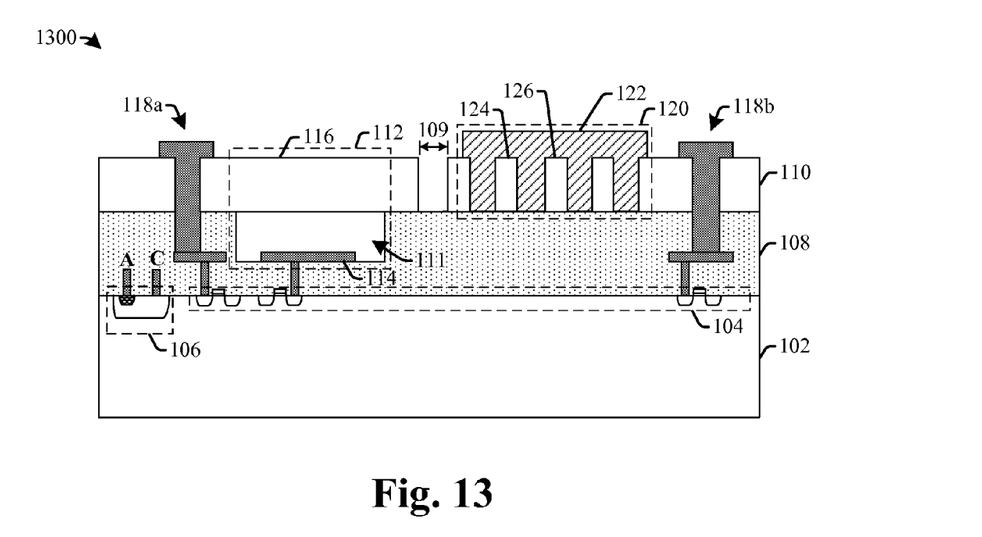

FIG. 13 illustrates some embodiments of a cross-sectional view 1300 of an integrated chip corresponding to act 714.

As shown in cross-sectional view 1300, a polymer 122 is formed over the first gas sensor electrode 124 and the second gas sensor electrode 126. The polymer 122 may be deposited over the substrate by way of a vapor deposition technique (e.g., physical vapor deposition, chemical vapor deposition, etc.). In some embodiments, the polymer 122 may comprise polyimide. In other embodiments, the polymer 122 may comprise polyaniline (PAni), polypyrrole (PPy) and poly (3,4-ethylenedioxythiophene) (PEDOT). After deposition, the polymer 122 may be selectively patterned to confine the polymer 122 to a position overlying the first gas sensor electrode 124 and the second gas sensor electrode 126.

Figure 14:
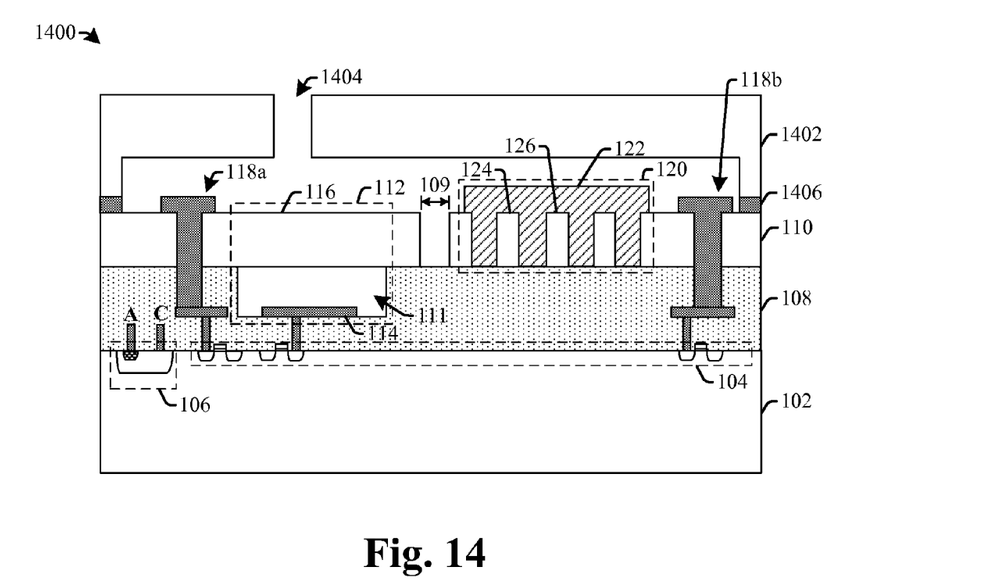

FIG. 14 illustrates some embodiments of a cross-sectional view 1400 of an integrated chip corresponding to act 716.

As shown in cross-sectional view 1400, a capping substrate 1402 is bonded to the MEMS substrate 110.

The capping substrate 1402 may be formed by selectively etching a substrate according to a first etching process to form a recess. The substrate is selectively etched within the recess to form an opening 1404 that extends through the capping substrate 1402. The capping substrate 1402 is then bonded to the MEMS substrate 110. In some embodiments, the capping substrate 1402 may be bonded to the MEMS substrate 110 by a eutectic bonding process that uses a bonding interface layer 1406 comprising a first material (e.g., Al, Cu, Ti, Ta, Au, Ni, Sn) arranged on an upper surface of the MEMS substrate and a second material (e.g., Ge, Si) arranged on a lower surface of the capping substrate 1402. In other embodiments, the capping substrate 1402 may be bonded to the MEMS substrate 110 by a direct bonding process.

Therefore, the present disclosure relates to a monolithic MEMS (micro-electromechanical system) device comprising a temperature sensor, a pressure sensor, and a gas sensor, and an associated method of formation.

In some embodiments, the present disclosure relates to a monolithic micro-electromechanical systems (MEMS) platform. The monolithic MEMS platform comprises a semiconductor substrate having one or more transistor devices and a temperature sensor. The monolithic MEMS platform further comprises a dielectric layer disposed over the semiconductor substrate. The dielectric layer has a cavity disposed within an upper surface of the dielectric layer. The monolithic MEMS platform further comprises a MEMS substrate arranged onto the upper surface of the dielectric layer and has a first section and a second section that is electrically disconnected from the first section. The monolithic MEMS platform further comprises a pressure sensor having a first pressure sensor electrode and a second pressure sensor electrode that are vertically separated by the cavity, wherein the second pressure sensor electrode comprises the first section of the MEMS substrate. The monolithic MEMS platform further comprises a gas sensor comprising a polymer disposed between a first gas sensor electrode comprising the second section of the MEMS substrate and a second gas sensor electrode.

In other embodiments, the present disclosure relates to a monolithic MEMS platform. The monolithic MEMS platform comprises a semiconductor substrate comprising one or more transistor devices and a temperature sensor. The monolithic MEMS platform further comprises a dielectric layer disposed over the semiconductor substrate and having a cavity disposed within an upper surface of the dielectric layer. The monolithic MEMS platform further comprises a plurality of metal interconnect layers arranged within the dielectric layer and comprising a first pressure sensor electrode extending along a bottom surface of the cavity. The monolithic MEMS platform further comprises a MEMS substrate comprising a conductive semiconductor material disposed onto the upper surface of the dielectric layer, wherein the MEMS substrate comprises a second pressure sensor electrode disposed over the cavity and first gas sensor electrode electrically isolated from the second pressure sensor electrode. The monolithic MEMS platform further comprises a polymer having a dielectric constant that varies depending upon a humidity of a surrounding ambient environment, which is disposed between the first gas sensor electrode and a second gas sensor electrode.

In yet other embodiments, the present disclosure relates to a method of forming a monolithic MEMS platform. The method comprises performing CMOS processes to form a temperature sensor and a plurality of devices within a substrate. The method further comprises forming a dielectric layer over the substrate, wherein the dielectric layer comprises a plurality of metal interconnect layers and a cavity arranged within an upper surface of the dielectric layer. The method further comprises bonding a MEMS substrate to the upper surface of the dielectric layer. The method further comprises patterning the MEMs substrate to concurrently define a second pressure sensor electrode for a MEMs pressure sensor and a first gas sensor electrode for a MEMS gas sensor. The method further comprises forming a polymer over the first gas sensor electrode.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A monolithic micro-electromechanical systems (MEMS) platform, comprising:
   a semiconductor substrate comprising one or more transistor devices and a temperature sensor;
   a dielectric structure disposed over the semiconductor substrate and having a cavity disposed within an upper surface of the dielectric structure;
   a MEMS substrate arranged onto the upper surface of the dielectric structure and having a first section and a second section that is electrically disconnected from the first section;
   a pressure sensor having a first pressure sensor electrode and a second pressure sensor electrode that are vertically separated by the cavity, wherein the second pressure sensor electrode comprises the first section of the MEMS substrate; and a gas sensor comprising a polymer disposed between a first gas sensor electrode within the second section of the MEMS substrate and a second gas sensor electrode, wherein the polymer extends from over the MEMS substrate to between sidewalls of the MEMS substrate.

2. The monolithic MEMS platform of claim 1,
wherein the cavity is defined by sidewalls of the dielectric structure coupled between the upper surface of the dielectric structure and a recessed surface of the dielectric structure facing away from the semiconductor substrate; and wherein the first pressure sensor electrode comprises a metal interconnect layer arranged onto the recessed surface of the dielectric structure at a position laterally between the sidewalls of the dielectric structure and vertically under the second pressure sensor electrode.

3. The monolithic MEMS platform of claim 1, wherein the first gas sensor electrode comprises a first comb-like structure and wherein the second gas sensor electrode comprises a second comb-like structure interdigitated with the first comb-like structure.

4. The monolithic MEMS platform of claim 1, wherein the polymer is disposed onto the first gas sensor electrode and wherein the second gas sensor electrode comprises a metal layer disposed over the polymer at a position vertically overlying the first gas sensor electrode.

5. The monolithic MEMS platform of claim 1, wherein the first section of the MEMS substrate is spatially separated from the second section of the MEMS substrate by way of a space.

6. The monolithic MEMS platform of claim 1, further comprising:
a first vertical interconnect structure laterally extending from the semiconductor substrate to the first section of the MEMS substrate; and
a second vertical interconnect structure vertically extending from the semiconductor substrate to the second section of the MEMS substrate.

7. The monolithic MEMS platform of claim 6, further comprising a capping substrate disposed over the MEMS substrate.

8. The monolithic MEMS platform of claim 7, further comprising:
a through-substrate-via (TSV) vertically extending from the first vertical interconnect structure through the capping substrate;
a redistribution layer electrically connected to the TSV and arranged within a protection layer disposed onto a side of the capping substrate opposing the MEMS substrate; and
a plurality of solder balls electrically coupled to the redistribution layer.

9. The monolithic MEMS platform of claim 1, wherein the MEMS substrate is set back from an outer edge of the semiconductor substrate and the dielectric structure, so as to expose a bonding area having an exposed a metal interconnect layer disposed within the dielectric structure.

10. The monolithic MEMS platform of claim 1, further comprising:
a through-substrate-via (TSV) vertically extending through the semiconductor substrate;

a redistribution layer electrically connected to the TSV and arranged within a protection layer disposed onto a side of the semiconductor substrate opposing the dielectric structure; and
a plurality of solder balls electrically coupled to the redistribution layer.

11. The monolithic MEMS platform of claim 1, wherein the first section of the MEMS substrate has a first thickness and the second section of the MEMS substrate has a second thickness that is different than the first thickness.

12. A monolithic MEMS platform, comprising:
a semiconductor substrate comprising one or more transistor devices and a temperature sensor;
a dielectric layer disposed over the semiconductor substrate and having a cavity disposed within an upper surface of the dielectric layer;
a plurality of metal interconnect layers arranged within the dielectric layer and comprising a first pressure sensor electrode extending along a bottom surface of the cavity;
a MEMS substrate comprising a conductive semiconductor material disposed onto the upper surface of the dielectric layer, wherein the MEMS substrate comprises a second pressure sensor electrode disposed over the cavity and first gas sensor electrode electrically isolated from the second pressure sensor electrode; and
a polymer having a dielectric constant that varies depending upon a presence of a liquid or gas in a surrounding ambient environment, which is disposed between the first gas sensor electrode and a second gas sensor electrode.

13. The monolithic MEMS platform of claim 12, wherein the polymer comprises polyimide.

14. The monolithic MEMS platform of claim 12, wherein the second gas sensor electrode comprises a metal material extending from the MEMS substrate to a position overlying the polymer.

15. The monolithic MEMS platform of claim 12, wherein the first gas sensor electrode comprises a first comb-like structure and wherein the second gas sensor electrode comprises a second comb-like structure interdigitated with the first comb-like structure.

16. The monolithic MEMS platform of claim 12, further comprising:
a first vertical interconnect structure laterally extending from the semiconductor substrate to the second pressure sensor electrode; and
a second vertical interconnect structure vertically extending from the semiconductor substrate to the first gas sensor electrode.

17. The monolithic MEMS platform of claim 12, wherein the MEMS substrate comprises doped amorphous silicon or doped polycrystalline silicon.

18. A method of forming a monolithic MEMS platform, comprising:
performing CMOS processes to form a temperature sensor and a plurality of devices within a substrate;
forming a dielectric structure over the substrate, wherein the dielectric structure surrounds a plurality of metal interconnect layers and a cavity defined by sidewalls of the dielectric structure coupled between an upper surface of the dielectric structure and a recessed surface of the dielectric structure facing away from the substrate, and wherein a first pressure sensor electrode for a MEMS pressure sensor comprises a metal interconnect layer disposed along the recessed surface and between the sidewalls of the dielectric structure;

bonding a MEMS substrate to the upper surface of the dielectric structure;
patterning the MEMs substrate to concurrently define a second pressure sensor electrode for the MEMs pressure sensor and a first gas sensor electrode for a MEMS gas sensor; and
forming a polymer over the first gas sensor electrode.

19. The method of claim 18, further comprising:
forming a vertical interconnect structure that vertically extend through the MEMs substrate to connect the first gas sensor electrode to one or more of the plurality of devices within the substrate.

20. The method of claim 18, further comprising:
bonding a capping substrate to a side of the MEMS substrate opposing the dielectric structure, wherein the capping substrate has sidewalls and an interior surface facing the MEMS substrate, which define a second cavity continuously extending from over the second pressure sensor electrode to over the first gas sensor electrode.

* * * * *